US006702575B2

(12) United States Patent
Hilliard

(10) Patent No.: US 6,702,575 B2
(45) Date of Patent: Mar. 9, 2004

(54) ORTHODONTIC ALIGNER AUXILIARY SYSTEM

(76) Inventor: Jack Keith Hilliard, 330 E. Highlands Dr., Lakeland, FL (US) 33813

( * ) Notice: Subject to any disclaimer, the term of this patent is extended or adjusted under 35 U.S.C. 154(b) by 22 days.

(21) Appl. No.: 10/115,413

(22) Filed: Apr. 3, 2002

(65) Prior Publication Data

US 2003/0190575 A1 Oct. 9, 2003

(51) Int. Cl.⁷ ............................... A61C 3/00
(52) U.S. Cl. ............................ 433/6; 433/18
(58) Field of Search ..................... 433/2, 6, 18, 24

(56) References Cited

U.S. PATENT DOCUMENTS

| | | | |
|---|---|---|---|
| 1,463,968 A | | 8/1923 | Petry |
| 2,257,709 A | | 9/1941 | Anderson |
| 2,467,432 A | | 4/1949 | Kesling |
| 2,479,780 A | * | 8/1949 | Remensnyder |
| 3,178,820 A | * | 4/1965 | Kesling |
| 3,407,500 A | * | 10/1968 | Kesling |
| 3,510,946 A | | 5/1970 | Kesling |
| 3,574,941 A | * | 4/1971 | Ritter |
| 3,724,075 A | * | 4/1973 | Kesling |
| 3,950,851 A | | 4/1976 | Bergersen |
| 3,991,471 A | | 11/1976 | Hoops |
| 4,055,895 A | * | 11/1977 | Huge |
| 4,505,672 A | * | 3/1985 | Kurz ........................... 433/6 |
| 4,591,341 A | | 5/1986 | Andrews |
| 4,755,139 A | | 7/1988 | Abbatte et al. |
| 4,793,803 A | * | 12/1988 | Martz ........................... 433/6 |
| 5,242,304 A | | 9/1993 | Truax et al. |
| 5,536,168 A | | 7/1996 | Bourke |
| 5,683,244 A | | 11/1997 | Truax |
| 5,692,894 A | | 12/1997 | Schwartz et al. |
| 6,217,325 B1 | | 4/2001 | Chishti et al. |
| 6,293,790 B1 | | 9/2001 | Hilliard |
| 6,299,440 B1 | | 10/2001 | Phan et al. |
| 6,309,215 B1 | | 10/2001 | Phan et al. |

FOREIGN PATENT DOCUMENTS

WO   WO 99/42055   * 8/1999

* cited by examiner

Primary Examiner—Ralph A. Lewis
(74) Attorney, Agent, or Firm—Dorr, Carson, Sloan, Birney & Kramer, P.C.

(57) ABSTRACT

A method and apparatus for orthodontic treatment employs a removable orthodontic aligner having a polymeric shell with a plurality of cavities shaped to receive teeth. A number of openings are formed that extend through the shell of the orthodontic aligner into a cavity. An orthodontic aligner auxiliary can then be secured to the opening in the shell of the orthodontic aligner to exert a therapeutic force on a tooth.

30 Claims, 7 Drawing Sheets

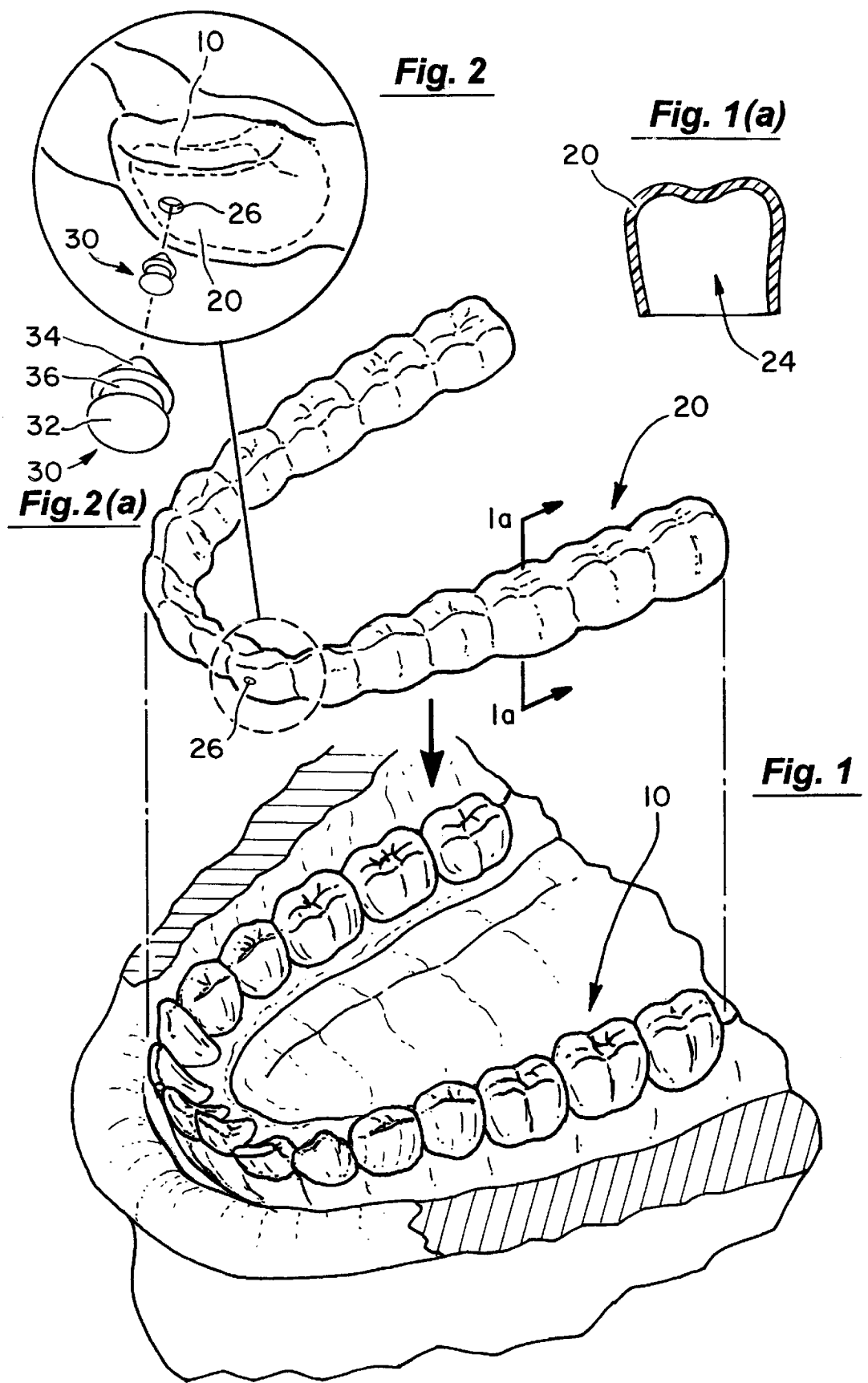

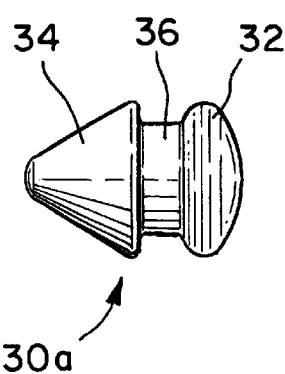 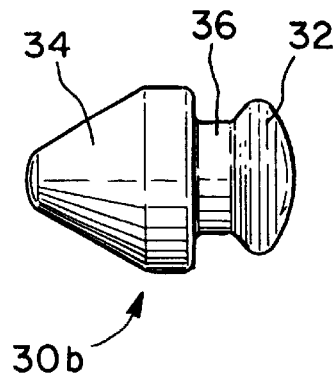 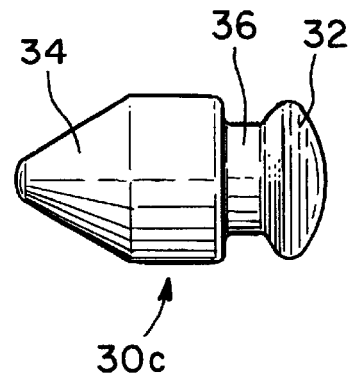
*Fig. 3(a)*     *Fig. 3(b)*     *Fig. 3(c)*
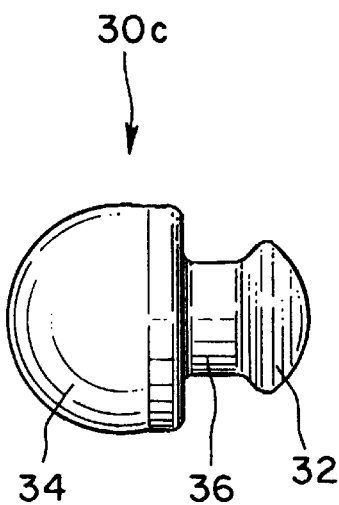 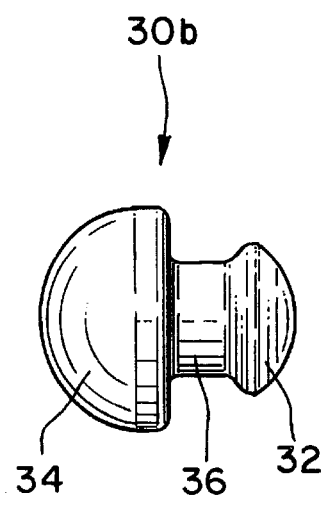 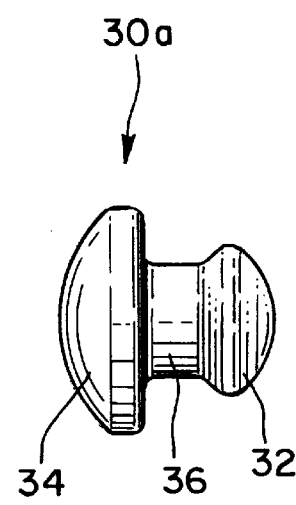
*Fig. 4(c)*     *Fig. 4(b)*     *Fig. 4(a)*

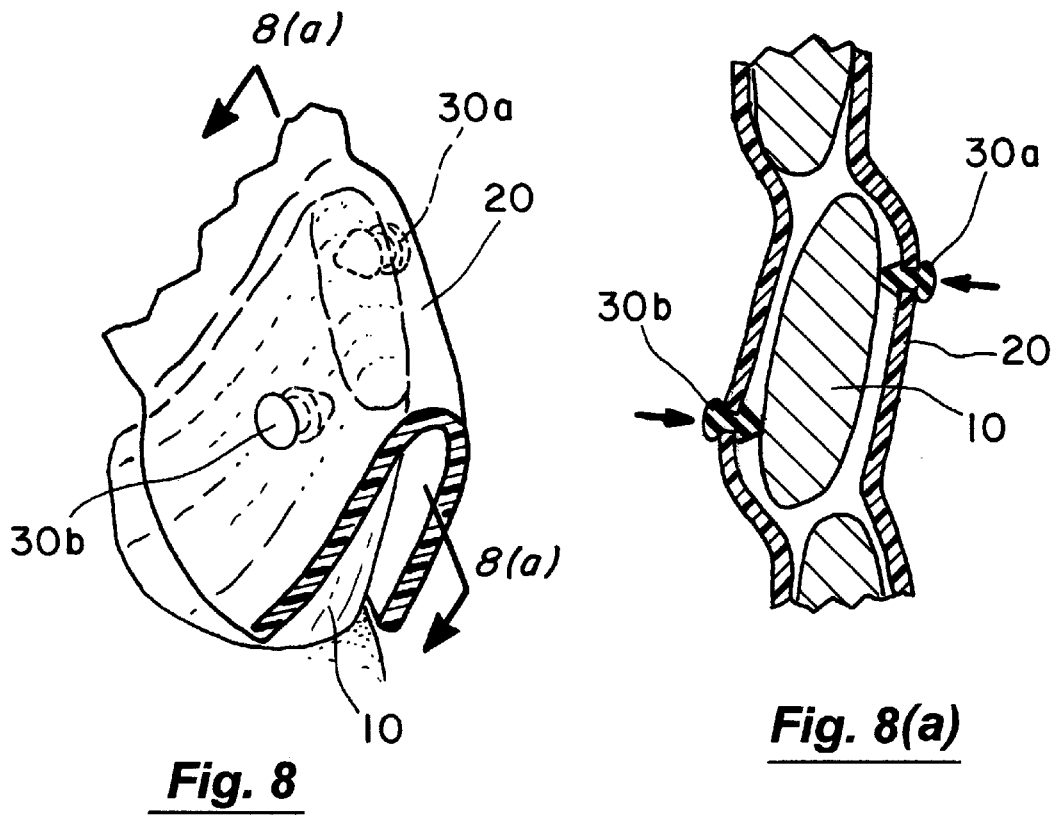
Fig. 8
Fig. 8(a)
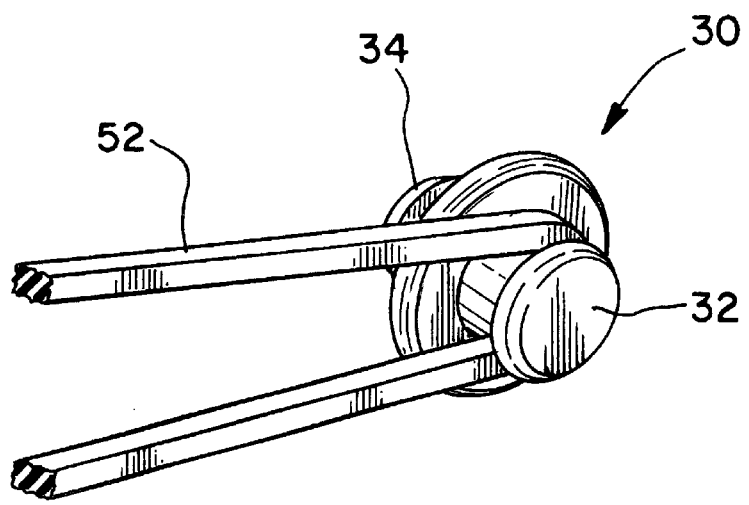
Fig. 9

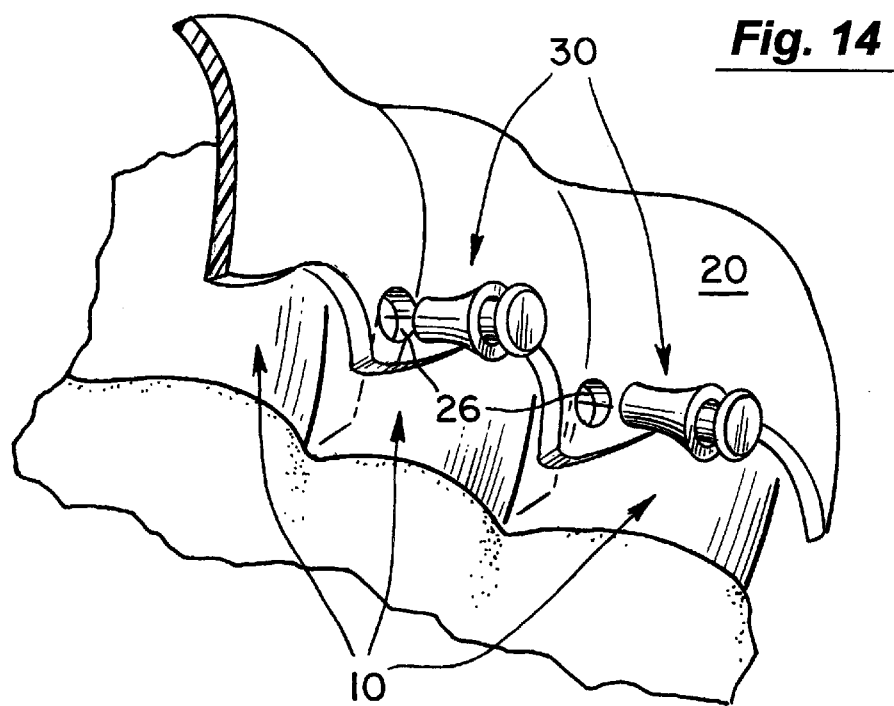
Fig. 14
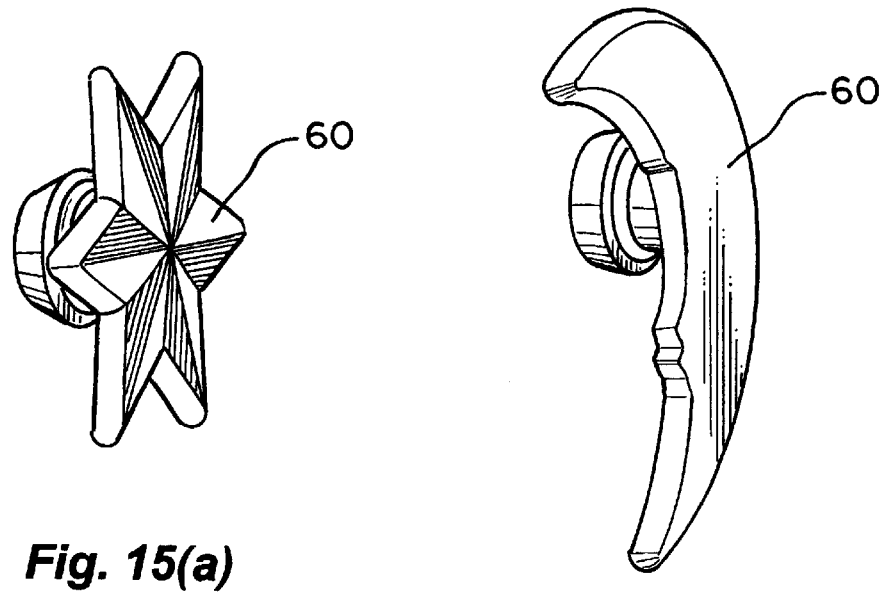
Fig. 15(a)
Fig. 15(b)

ORTHODONTIC ALIGNER AUXILIARY SYSTEM

BACKGROUND OF THE INVENTION

1. Field of the Invention

The present invention relates generally to the field of orthodontic appliances. More specifically, the present invention discloses a method and apparatus of orthodontic treatment in which any of a variety of orthodontic aligner auxiliaries can be used in conjunction with a removable aligner for orthodontic treatment.

2. Statement of the Problem

In the field of orthodontics, treatment is currently accomplished through the use of a wide range of hardware options available to the practitioner. Taken to a simplest form, these options can be categorized into two groups. The first group is conventional braces, which are based on tooth-mounted mechanical systems intended to reposition a patient's teeth. The other group includes various types of orthopedic appliances that act to elicit a more physiological or skeletal response. The orthopedic approach is directed not only to repositioning of an orthodontic patient's teeth, but also to attaining a corrected and stable balance between the jaws, the facial musculature and the bony structures of the face. In practice, orthodontic correction is typically accomplished through a combination of these two approaches where first a patient's skeletal relationships will be brought into a more harmonious and corrected balance, and once corrected in that manner, the teeth will then be moved into desired final aesthetic positions and desired relationships using conventional braces.

Many auxiliary treatment systems have been developed that generally serve to augment or support the two basic approaches described above. Such auxiliary systems include devices known as retainers, face bows, holding arches, reverse-pull headgear, transpalatal arches, rapid palatal expanders, lingual arch developers, mandibular advancers, lip bumpers and the like. In most cases, such auxiliary treatment devices serve progressively during specific sub-phases of treatment and serve to expedite one treatment objective that must be accomplished before another can begin.

As the science of orthodontic treatment and the related armamentarium has matured, some particularly skilled orthodontists have become so adept at using such auxiliary support systems that their use has been expanded to become a central means of a complete treatment methodology. Many such auxiliary support systems have been commercialized and thus provide the orthodontic profession with many treatment tools, methods and options usefully bolstering treatment methods using conventional "braces" and the orthopedic approaches.

One such orthodontic auxiliary support system to which the present invention is directed is broadly known in orthodontics as the orthodontic tooth positioner. Orthodontic tooth positioners can be characterized as being generally U-shaped, conforming to the shape of the dental arches and formed of a soft, flexible or resilient material. A trough is formed along the generally U-shaped configuration of a tooth positioner, which consists of multiple depressions, each depression being negatively formed to intimately contact and positively accept a corresponding tooth. When placed in the patient's mouth, a tooth positioner typically spans and intimately accepts all of the teeth of an upper or lower arch of a patient and in doing so typically covers the entire crown of the teeth. Tooth positioners usually do not extend beyond the gingival margin of the teeth and therefore do not typically contact the adjacent soft tissue or the gums.

Generally speaking, positioners used in the past tended to be integral, i.e. formed from a single mass of natural vulcanized rubber material containing two troughs; one of which is upwardly facing for engaging the upper teeth and the other oriented downward for engaging the lower teeth. More recently, tooth positioners are more commonly formed as a set of two separate positioners, with one of a set being adapted to the upper arch and the other independently adapted to the lower arch. Other types of special-purpose positioners are sometimes formed to engage just on side or one quadrant of an arch.

The orthodontic tooth positioner, and methods for forming them were first disclosed in the orthodontic literature in 1946 by H. D. Kesling, a well-known and influential orthodontist of that day. Based on the work of Kesling, positioner-based therapy methods were developed and commercial support for those doctors using positioners was provided by orthodontic laboratories. Kesling published a number of articles extolling the virtues of tooth positioners, describing them as providing effective functional tooth-moving forces without any interference from bands, brackets or wires.

As stated above, both today and in the past, orthodontists choosing to treat patients with tooth positioners typically rely on the services of an orthodontic laboratory to form positioners for their patients. Orthodontic laboratories provide service for the custom-fabrication of a tooth positioner for an individual patient according to a treatment plan and a prescription provided by the attending orthodontist or dentist. For this process, a poured and cured stone replica of a patient's initial malocclusion is provided by the doctor for the laboratory's use.

The dental technicians within a laboratory first modify the stone model by cutting the mal-positioned teeth free of the model and the adjacent teeth. Next, a technician repositions the teeth on the model semi-rigidly into desired, ideal positions as specified by the doctor and as determined by the doctor's diagnosis and subsequent treatment plan. After the stone model has been modified or "corrected" in this manner, the model will be positioned within a tooth positioner-forming machine where through the simultaneous use of air pressure, vacuum and heat, a sheet of thermo-formable vinyl or other rubber-like or thermo-formable elastomeric material is "sucked-down" over the stone model (s). After forming the positioner in this manner, excess material is trimmed from the positioner, and it is sent back to the orthodontist's practice and an appointment is scheduled to seat the positioner in the mouth of the patient.

In the past, the process of forming a tooth positioner has been much more labor intensive. Rather than "sucking down" a sheet of thermo-formable material, it was necessary to first create a mold and then cast thermosetting materials or other materials that required heat, pressure and time to cure.

As can be appreciated, a completed laboratory-produced tooth positioner reflects the teeth in improved positions and orientations compared to the actual positions and orientations of the teeth at the beginning of a patient's treatment. When a new positioner is first placed on the patient's mal-occluded teeth, each tooth will tend to distort and load the elastomeric material adjacent to each tooth impression formed in the positioner. With the positioner fully seated on the patient's arches, the material adjacent to each tooth will become elastically loaded, and within the elastomeric material of the positioner, energy will have been stored. Essentially, it is the slow dissipation of that stored energy, over time, that provides the gentle, continuous biologically effective force to which the bone underlying the tooth will respond, and the tooth will move into positions according to the gentle urging of the positioner.

As described, positioner-based treatment as first introduced by Kesling in the late 1940's. The positioners as taught by Kesling were based on relatively inelastic and relatively hard natural rubber materials of the day and therefore such positioners exhibited insufficient elasticity to accomplish primary tooth moving objectives. Such appliances were generally limited to effecting minor tooth movement near the end of treatment and for a period of time they could also be used as a post-treatment retainer of sorts. In order for the tooth positioners used by Kesling to serve as the primary tooth moving treatment modality, the laboratory step involving the physical repositioning of the "stone" teeth by the technician had to done in multiple, incremental steps, and multiple, incremental positioners were required. Each incremental step represented only partial movement toward ideal tooth positions. In addition to the constraints of requiring extensive coordination between the doctor and the laboratory, laboratory processing of the early positioners required a time consuming sequence of casting and heat curing. The total cost involved with such a complex process was acknowledged by Kesling as being prohibitive. As Kesling understood, the degree or extent to which a single tooth positioner can be used as the primary method for orthodontic treatment is dependent on the mechanical properties of the material from which the positioner is formed. Kesling lamented the limitations of his positioners but predicted that in the future, through use of then undeveloped materials, tooth positioner based therapy would hold great potential for serving as a primary treatment means.

Driven by both the potential and the limitations of tooth positioners, various substitutes for hard natural rubber were investigated by research groups as well as clinicians wishing to advance the tooth positioner-based treatment philosophy. In the United States, during the 1970's Cottingham, Warunek, Strychalski and Cunat all investigated medical grade polydimethyl silicate, a material known generically as silicone rubber or silicone elastomer. In Japan, Nishiyama, Kamada, and Horiuchi investigated dimethylvinyl siloxy polydimethylsiloane with a chloroplatinic acid catalyst, generically known as LTV vinyl silicone. Another Japanese researcher; Osama Yoshii developed a tooth positioner treatment methodology using the controlled variable durometer characteristic of LTV vinyl silicone and thus formed progressive positioners based on incremental increases in hardness of a series. Being generally transparent, non-staining, and hygroscopic, the engineered elastomers developed by these investigators solved some of the problems associated with Kesling's original tooth positioner. To a greater degree, tooth positioners formed from these new materials could be counted on as a dependable means for correcting orthodontic malocclusions. These softer, more resilient materials served in the mouth without discomfort, but still required extensive laboratory casting processes to form them. Nonetheless, as a result of the research described above, a group of elastomeric material systems are currently available for use in forming clear, highly elastic tooth positioners as well as a number of other common orthodontic appliances.

Generally, tooth positioners are popular with young, and perhaps self-conscious orthodontic patients in that they have attributes that reduce social or self-image concerns associated with their appearance during treatment. One fundamental attribute of tooth positioners is that they are removable by the patient, and since in some cases orthodontists prescribe that positioners be worn only after school and during sleep, teenage orthodontic patients have the option of removing their appliances. This allows teenage, as well as adults to avoid speech problems and personal appearance concerns that are commonly associated with conventional braces.

Beginning generally in the early 1980's, a general increased awareness of the advantages of tooth positioners by orthodontists again drove increased interest. The orthodontic community also noted the commercial success of both the laboratories that produced tooth positioners and the manufacturers and distributors who provided the catalyzable materials as well as the popularity of such appliances with patients. In particular, orthodontists realized that the original vision of Kesling, who first articulated the many potential advantages of positioner therapy, had been to a degree realized through the use of the more resilient modern materials.

Tooth positioners and tooth positioner-based orthodontic therapy evolved into its current status through the use of yet other new materials and new, simpler and less labor-intensive means of forming tooth positioners. As described above, the use of thin sheets of various thermo-formable plastics including vinyl and olefin-type materials has been adopted for current tooth positioners. This, along with an efficient forming process involving the rapid use of pressure, vacuum and heat, has replaced the prior molding and casting processes. Polypropylene in particular exhibits an ideal combination of properties. Particularly in its higher molecular density ranges, polypropylene exhibits desirable mechanical properties in that it is nearly transparent, and in the mouth it is non-reactive chemically and thoroughly biocompatible. One commercial source for the new positioner material is Raintree Essix, New Orleans, La. The use of these materials, including polypropylene in sheet form and in thicknesses of about 1 mm (before thermoforming), eliminates the time-consuming steps of mixing, catalyzing and curing (in some cases heat-curing in a pressure flask) as was required by the outmoded natural rubber, medical-grade urethane, silicone and vinyl silicone series materials. Being thermo-formable, positioners can be easily "sucked down" over the patient's reset stone model using heat, pressure and vacuum simultaneously. Since the processing of the new type of thin positioner is so markedly simplified, some orthodontists have even found it practical to form them directly in the orthodontic office, thus avoiding the cost, time and administrative tasks required by laboratory processing. To distinguish between the older types of positioners formed from medical-grade urethane, silicone or vinyl silicone materials, current thin, thermo-formed positioners are generally referred to as "aligners."

Once formed, aligners are typically trimmed to closely match the gingival margins of the teeth. When in position in a patient's mouth, current aligners are virtually invisible, and unnoticeable. Being thin, they do not appreciably interfere with speech as the older, much more bulky urethane, silicone and vinyl silicone-formed versions tended to do. Because of the combined advantages sited previously for tooth positioners combined with the thin, non-bulky, low profile afforded by aligners, aligners are even more readily tolerated by patients and are currently popular with orthodontists.

To demonstrate the general integration and importance of aligner-based treatment methods in the orthodontic field, a combination of current aligner-based therapy philosophies and digital imaging/computer-driven rapid prototyping methods have resulted in the emergence of a significant commercial development described by U.S. Pat. No. 5,975,893 (Chishti et al.). A methodology is taught by Chishti et al. in which multiple aligners are formed for a patient and each upper and lower set of aligners is worn for a set period of time (e.g., about two weeks). Progressive sets of aligners are provided in which each set more aggressively biases a patient's teeth toward an ideal occlusion. Orthodontic patients undergoing such progressive treatment may typically wear from between 15 to 25 sets of progressive aligners. Over a period of time, the sequential and progressively biased positioners move teeth from their initial maloccluded positions to a near finished and corrected state. This progressive aligner-based program is commercially offered to the orthodontic professional and is also marketed directly to the public by Align Technologies of Sunnyvale Calif. under the name "Invisalign." The Invisalign® program is promoted as "invisible braces" and as being a clear alternative to conventional braces.

Aligners, and the commercial fabrication of them is not limited to Align Technologies. Most orthodontic laboratories routinely form aligners according to prescriptions provided by orthodontists. Aligners also continue to be formed within the orthodontic offices. Even though not part of a progressive system such as the Invisalign® program, such laboratory or in-office-produced aligners perform a wide range of useful treatment functions including correction and retention. For those doctors opting to form their own aligners, methodologies taught by U.S. Pat. No. 5,692,894 (Schwartz et al.) provide one chair-side means of modifying previously formed aligners as may be required by the needs of any one patient.

U.S. Pat. No. 6,293,790, by the present inventor likewise provides a chair-side system of heated pliers useful for activating aligners as required as a patient's treatment progresses. The heated pliers exploit the thermoformable characteristic of the aligner material and permit them to be locally modified or activated.

Aligner-based therapy is an important and popular treatment modality used in orthodontics today. However, even though commercially successful, aligners still fall somewhat short of Kesling's original vision of being capable of fully treating the majority of patients presenting for orthodontic treatment. These remaining limitations can be seen for example in the fact that cases acceptable for the Invisalign® program must fall within the minor to moderate category in terms of severity of the malocclusion in order for aligners of the Invisalign® program to be effective. Patients exhibiting significant crowding, deep or open bites or excessively narrow occlusions present problems that are beyond the correction capabilities of present aligners. Because of this, for the majority of cases, aligners are still used in conjunction with conventional braces, or used at the end of treatment to accomplish a final aesthetic positioning of the teeth.

As can be appreciated, an individual tooth received within an intimately contacting, but desirably-biased recess or cavity formed within the polymeric shell of an aligner is urged to move in an orthodontically desirable net-vector direction by the slight positional biasing of the cavity. As previously described, as the aligner is positioned on any particular tooth, the difference between the position of the actual tooth, and the repositioned cavity of the aligner tends to load the polymeric shell material in regions just adjacent to the cavity. The stored energy thus imparted into the elastomeric material of the aligner slowly dissipates over time as the bone underlying the tooth physiologically responds to such therapeutic forces. The various corrective, therapeutic forces that are translated to the tooth in this manner can be characterized as: tipping the tooth in terms of torque; tipping the tooth in terms of angulation; rotating the tooth about its central axis; as well as subtle intrusive and in some cases, extrusive forces. Depending on the objectives of the treatment, some teeth may be expected to move bodily through the underlying bone and the gums into completely new locations along a patient's arches.

When treating a patient's teeth using an aligner, the effectiveness or intensity of these therapeutic forces decreases as treatment progresses. For instance, as treatment progresses the teeth will comply with the aligner and move as directed. After a tooth has moved to any significant degree toward its desired position, the energy stored within the resilient elastomeric shell of a conventional aligner will be correspondingly reduced and partially spent. Stated differently, as the aligner accomplishes its function of moving the teeth, the forces that it is capable of exerting on the teeth may drop off rapidly. During conventional aligner therapy, when treatment progresses to the point at which the aligner can no longer generate a sufficient level of therapeutic force that is above a minimum physiological threshold needed for tooth movement, the teeth will simply stop moving. For several reasons, such a situation is very undesirable. Traditionally, at such a point in treatment, a practitioner must arrange to have a new aligner formed, either within his office or by a support laboratory. In either case, the forming of a new aligner requires that impressions of the patient's teeth be taken again, and a new stone model made from the impressions, all of which involve attendant delay and expense. From the patient's point of view, this typically involves the inconvenience and expense of a separate appointment.

3. Solution to the Problem

In contrast to the prior art discussed above, the present invention employs orthodontic aligner auxiliaries that can be secured to openings in an aligner or other removable appliance to exert therapeutic forces on selected teeth. This enables aligners to used in treatment a much wider range of orthodontic cases and in treatment of orthodontic cases that are more severe. In addition, the orthodontic aligner auxiliaries can be removable or adjustable. This enables the therapeutic forces to be maintained, progressively changed, or reactivated over the course of treatment to significantly expand the capabilities of current aligner-based therapy and address the limitations discussed above.

SUMMARY OF THE INVENTION

This invention provides a method and apparatus for orthodontic treatment employing a removable aligner having a polymeric shell with a plurality of cavities shaped to receive teeth. A number of openings are formed that extend through the shell of the aligner into a cavity. An orthodontic aligner auxiliary can then be secured to the opening in the shell of the aligner to exert a therapeutic force on a tooth.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is an exploded perspective view of a patient's lower teeth 10 and a removable orthodontic aligner 20 with an opening 26.

FIG. 1(a) is a cross-sectional view of the orthodontic aligner 20 taken through one of its cavities 24, FIG. 2 is an exploded detail perspective view of the opening 26 in the orthodontic aligner 20 and an orthodontic aligner auxiliary 30.

FIG. 2(a) is a front perspective view of the orthodontic aligner auxiliary 30 in FIG. 2.

FIGS. 3(a) through 3(c) are side elevational views of a progressive series of orthodontic aligner auxiliaries 30a–30c with tapered tips 34.

FIGS. 4(a) through 4(c) are side elevational views of a progressive series of orthodontic aligner auxiliaries 30a–30c with rounded tips 34.

FIG. 8 is a detail perspective view of a portion of an aligner 20 with two orthodontic aligner auxiliaries 30a and 30b that exert a couple on a tooth 10.

FIG. 8(a) is a horizontal cross-sectional view of an aligner 20 with two orthodontic aligner auxiliaries 30a and 30b that exert a couple on a tooth 10, corresponding to the FIG. 8.

FIG. 9 is a detail perspective view of an aligner auxiliary 30 used to anchor an end of a rubber band 52.

FIG. 14 is an exploded detail perspective view of an embodiment of the present invention in which orthodontic aligner auxiliaries 30 extend into the interproximal spaces between teeth 10 to exert a retentive force holding the aligner 20 in place.

FIGS. 15(a) and 15(b) are front perspective views of embodiments in which the orthodontic aligner auxiliaries include ornamental or decorative designs.

DETAILED DESCRIPTION OF THE INVENTION

Figure 5:
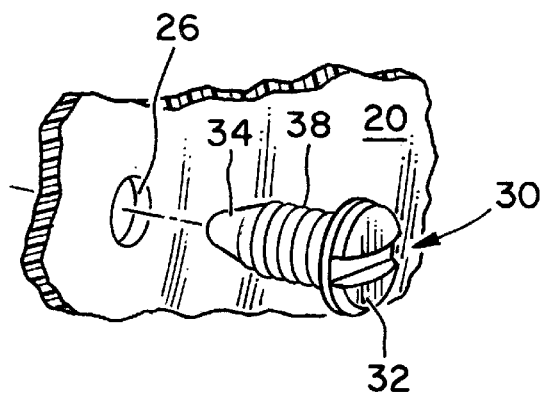
FIG. 5 is a detail perspective view of a threaded orthodontic aligner auxiliary 30 having a slotted head 32.

Turning to FIG. 1, an exploded perspective view is shown of a patient's lower teeth 10 and a removable orthodontic aligner 20. For the purposes of this discussion, a removable aligner of the type marketed under the Invisalign® brand is depicted in FIG. 1. However, it should be understood that other types of removable orthodontic aligners and positioners could be substituted. In particular, the removable aligner 20 has a polymeric shell with a plurality of cavities 24 to receive the patient's teeth 10, as illustrated in FIG. 1(a). The aligner 20 can be used to engage the patient's upper teeth, lower teeth, or a subset of either of these.

A number of openings 26 extend into the shell of the aligner 20 from selected cavities 24. These openings 26 can be formed during the molding process for the aligner 20 or subsequently created by the practitioner. In the preferred embodiment of the present invention, the practitioner creates openings at desired locations in selected cavities 24 using a hand-held instrument to pierce the shell of the aligner 20. An opening 26 can either extend completely through the shell or extend only partially into the shell from its interior surface depending on the type of orthodontic aligner auxiliary 30 to be inserted into the opening 26, as will be discussed below.

FIG. 2 is an exploded detail perspective view of an orthodontic aligner auxiliary 30 being inserted into an opening 26 in an aligner 20. The embodiment of the orthodontic aligner auxiliary 30 shown in FIG. 2(a) is a "tack" having a head 32, an opposing tapered tip 34, and recessed circumferential groove 36 between the head 32 and tip 34. The dimensions of the tip 34 and groove 36 are selected so that the tip 34 can be pushed through the opening 26 in the aligner 20 by application of a nominal axial force. The tack 30 can be made of a resilient polymer so that the tip 34 re-expands to its normal size after passing through the opening 26 in the aligner 20. In contrast, the dimensions of the head 32 of the tack 30 are selected so that it will not readily fit through the opening 26. Thus, after insertion of the tip 34 through the opening 26, the head 23 and tip 34 are on opposing sides of the aligner 20 and thereby secure the orthodontic aligner auxiliary 30 to the opening 26. For example, depending on the designer's choice of materials and dimensions, the tack 30 can be secured by a snap fit or a friction fit with the opening 26. The direction of insertion of the tack 30 is also a matter of design choice. The tip 34 of the tack 30 can be inserted from the outside of the aligner 20 so that the head 32 will be located on the exterior of the polymeric shell and the tip 34 will contact the tooth 10 to exert a therapeutic force on the tooth when the aligner 20 is in placed in the patient's mouth. Alternatively, the tip 34 can be inserted from the inside of the aligner 20 so that the head 32 will be located on the interior of the shell and will contact the tooth 10.

The practitioner can activate an aligner 30 by performing the following steps: With the aligner 30 seated on the patient's teeth, the configuration of the aligner will be visually assessed by the doctor on a tooth-by-tooth basis to identify the most mechanically-advantageous points at which to impinge additional corrective forces. Temporary marks will be placed on the polymeric shell corresponding to those identified points and the aligner 20 is then removed from the patient's mouth. The doctor will then pierce the aligner 20 at the identified and marked points using a pliers-mounted punch die. The pliers will create openings 26 of precise dimensions through the polymeric shell of the aligner 20. An orthodontic aligner auxiliary 30 can then be secured in the opening 26 of the aligner 20, in a snap-fit fashion, for example, and thus will be securely retained in the opening 26. For example, retention of the orthodontic aligner auxiliary 30 in the aligner 20 can be achieved by means of a precise sizing relationship of a circumferential groove 36 in the shank of the orthodontic aligner auxiliary 30 and the opening 26 formed through the polymeric shell. With the orthodontic aligner auxiliary 30 positioned thusly, the tooth-contacting tip 34 of the orthodontic aligner auxiliary 30 will then extend into the interior of a cavity 24 in the polymeric shell of the aligner 20. Multiple orthodontic aligner auxiliaries 30 can be retained in the polymeric shell of the aligner 20 and each cavity 24 of the aligner 20 may have one or more such devices 30 projecting into it, if necessary.

Other embodiments of the orthodontic aligner auxiliary 30 employ other means of retention as described below but each of these can be also accomplished solely, or augmented by adhesive bonding. Bonding of the orthodontic aligner auxiliary 30 onto or into the polymeric shell of a removable aligner 20 requires the use of an orthodontic adhesive system and requires both the polymeric shell and the orthodontic aligner auxiliary 30 be formed of a material capable of cross-linking or polymerizing with the adhesive system. For example, orthodontic aligner auxiliaries 30 may be formed from FDA-sanctioned food grade polycarbonate (Lexan) and the polymeric shell may also be thermo-formed from polycarbonate. An acrylic monomer adhesive system based on liquid and powder components, where the liquid contains a borane catalyst would provide the needed bonding characteristics. Adhesive systems based on a liquid/paste system consisting of styrene monomers and diglycedal methacrylate would likewise function but may require that the polycarbonate bonding surfaces be pre-treated with a conditioner consisting of the clear liquid component of such a system. Urethane dimethacrylate systems based on a photo-initiator (light cure) would also provide suitable bonding characteristics. Other well-known thermoformable dental materials other than polycarbonate may likewise provide adequate bonding characteristics and other adhesive systems used in dentistry and orthodontics may likewise serve the intended bonding function.

Whether activating an aligner to exert extra force on specific teeth, or reactivating an aligner, the aligner 20 with its orthodontic aligner auxiliaries 30 are first installed in the patient's mouth. In doing so, the aligner 20 is pushed down to its fully seated position on the patient's arches. The tooth-contacting tips 34 of the orthodontic aligner auxiliaries 30 contact the various mal-positioned teeth 10 at pre-identified points. Since the tip 34 of each orthodontic aligner auxiliary 30 extends into the interior of a cavity 24 of the aligner 20, and since those tips 34 first contact the teeth 10 as the aligner 20 is seated, they positively hold the adjacent material of the aligner 20 back from contact with the tooth 10 and thereby create space between the inner walls of a cavity 24 and the surface of a particular tooth 10. The region of the aligner 20 adjacent to the orthodontic aligner auxiliary 30 must distort and stretch to accommodate the space created. In doing so, the polymeric material of the aligner 20 is loaded so that energy is stored within the shell material. In the case of a reactivated appliance, the original aligner 20 is then in a reactivated condition and once again capable of imparting physiologically effective forces on the teeth 10 to move them in intended directions according to a treatment plan. In the case of a new aligner 20, it is in a modified condition, capable of delivering higher and more effective forces than it would be capable of alone.

Orthodontists have investigated the relationship between the interval between patient visits and the amount of corrective response that patients typically demonstrate during any set interval of time. Based on this investigation, orthodontists generally establish an interval of about six to eight weeks between a patient's appointments. In the case of a patient being treated with aligner-based therapy, it is possible for aligners to accomplish sufficient correction in less than this time interval. In such a case it is therefore probable that an aligner may undesirably dissipate its force-generating capabilities in less than a six to eight week interval. To avoid having to schedule more frequent appointments and the fabrication of additional aligners, a series of orthodontic aligner auxiliaries 30 (or tacks) may be given to the patient along with the orthodontist's instructions on how to remove and install them in an aligner 20 unassisted, at home. The tapered features of the heads 32 of the orthodontic aligner auxiliaries 30 allow their removal from an aligner 20 using a household fingernail trimmer. Therefore, it is not unreasonable to expect a patient to successfully use such a trimmer to cut off the externally-extending head 32 of an orthodontic aligner auxiliary 30, thereby permitting it to be removed from the aligner 20 and replaced with another.

In cases where the aligner 20 has been previously activated through use of the present invention, a patient may be instructed to install a series of tacks 30a–30c of progressive lengths, as shown in FIGS. 3(a) through 3(c), thus enabling the exertion a progression of therapeutic forces on a patient's teeth.

Another means of exerting a progression of corrective therapeutic forces on a tooth is achieved by using a progression of tack elasticities. As attributed above to Osama Yoshii, and based on the controlled variable durometer characteristic of LTV vinyl silicone for example, such a patient-activated methodology is possible. For this, a series of tacks can be produced in a material capable of exhibiting a range of durometer hardnesses such as 45, 60 and 80 Shore B hardnesses, referred to as "soft", "medium" and "hard". Since such devices could inherently have larger, more spherically shaped tooth contacting features, as shown in FIGS. 4(a) through 4(c), a practitioner or patient would insert the orthodontic aligner auxiliary 30 from inside a cavity 24.

As described, one aspect of the present invention involves a series of lengths such as short, medium and long, and another involves a progression of hardnesses. Both of these progressions can usefully be combined in one series. For convenience, different stages of any such progression could include orthodontic aligner auxiliaries 30 that are formed from a color-coded material for easy coordination of their use as the patient progresses from one to the next.

Alternatively, a tack 30 could be formed with a series of circumferential grooves or ribs spaced along its longitudinal axis. The force exerted by the tack 30 on a tooth 10 can be adjusted by varying the pushing or pulling the tack 30 so that a different groove and/or ribs engage the shell of the aligner 20.

Other embodiments of the orthodontic aligner auxiliary are possible. For example, a tack having an enlarged head and a short shaft (not shown) could be inserted into an opening from the inside of the aligner. The shaft of the orthodontic aligner auxiliary could be bonded to the opening or held in place by friction. The head protrudes into a cavity of the aligner and exerts a therapeutic force on a tooth when the aligner is installed in the patient's mouth. In this embodiment, the opening need not necessarily extend completely through the shell of the aligner. As previously discussed, a progression of forces can be exerted on a tooth by means of a series of tacks of varying length or elasticity.

Figure 6:
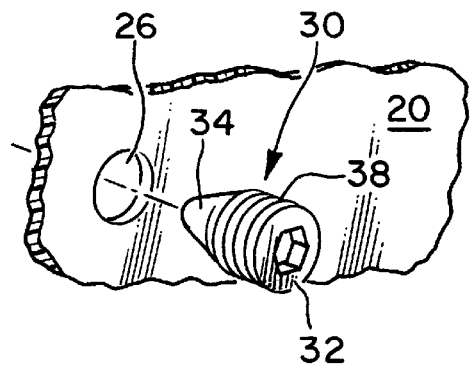
FIG. 6 is a detail perspective view of a threaded orthodontic aligner auxiliary 30 having a head 32 with a recess to accommodate an Allen wrench.

Another embodiment of the present invention that facilitates both at-home patient activation and chair-side activation can be seen in the following. First, an opening 26 is created in the polymeric shell extending into a cavity 24, as previously discussed. An orthodontic aligner auxiliary 30 having a threaded shaft 38 is then screwed into the opening 26 in the shell, so that it engages the inside surface of the opening 26 in a secure, self-threading and adjustable manner, as illustrated in FIGS. 5 and 6. For example, FIG. 5 shows a threaded orthodontic aligner auxiliary 30 having a slotted head 32 adapted for receiving a conventional screw driver. FIG. 6 shows a threaded orthodontic aligner auxiliary 30 having a head 32 with a recess to receive accommodate an Allen wrench. Other types of hand-held activation instruments could be readily substituted.

Figure 7:
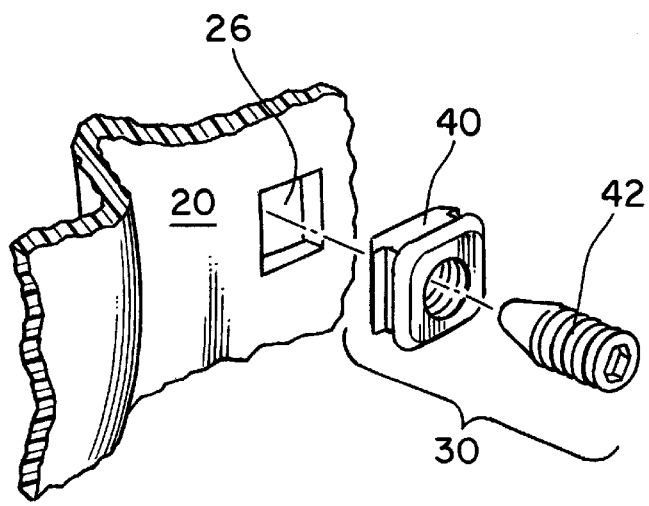
FIG. 7 is an exploded detail perspective of an orthodontic aligner auxiliary 30 having a nut 40 that snaps into an opening 26 of an aligner 20, and a screw 42 that threads into the nut 40.

Yet another embodiment involving an adjustable two-part orthodontic aligner auxiliary 30 that facilitates both at-home patient activation and chair-side activation can be seen in FIG. 7. First a generally rectangular opening of predetermined dimensions is created through the polymeric shell of the aligner 20. A "nut" component 40 is inserted to engage the opening. A tapered portion of the nut 40 extends through the opening 26 in the shell and the nut 40 is retained in the square groove located around the periphery of the nut 40 between the tapered section and the head or flange of the nut 40. The nut 40 has a threaded hole. A screw 42 is then threaded into the nut 40, as shown in FIG. 7, so that the tip of the screw 42 extends into the cavity 24 of the aligner 20 and contacts a tooth 10. The degree of force exerted by the screw 42 can be periodically adjusted by rotating the screw 42 relative to the nut 40 by means of a hand-held activation instrument such as a screwdriver or Allen wrench.

Certain teeth will naturally be positioned farther from their desired positions than other teeth, or stated differently, certain teeth will require greater correction than others. In such cases, a doctor may first identify those teeth requiring the greatest degree of correction. In the instance of a severely distal-lingually rotated maxillary lateral right for example, one orthodontic aligner auxiliary 30a may be installed in the cavity of a polymeric shell so as to be located near the incisal edge of the crown of the tooth 10, and near the mesial edge of the tooth 10. This tack 30a would pass through the aligner 20 from the labial side of the generally trough-shaped polymeric shell. A second orthodontic aligner auxiliary 30b may be inserted through the lingual side of the same cavity, as shown in FIGS. 8 and 8(a). Such a lingually-positioned tack 30b may also be located near the incisal edge of the tooth 10, but near its distal edge. In this way, the aligner, when seated, creates a rotational coupling of two forces created by the two tacks 30a and 30b working in concert, which can very aggressively impart a significantly higher rotational force than can be achieved by one tack acting alone. Further, through the availability of a system of progressive lengths or progressive elasticities, such couple-based progressive therapeutic forces can be part of a patient-activated modality between appointments. In treatment, combinations of orthodontic aligner auxiliaries can generate various types of therapeutic forces that can be directed to individual mal-positioned teeth in a manner where rotational correction can be accomplished with a mesially-directed or lingually-directed emphasis or bias, thus providing the practitioner with a comprehensive means of differentially repositioning the teeth. For example, the mesial labial device described in the example of couple-type forces may be a "short"; whereas the lingual distal device may be a "long". In this manner, the practitioner may be able to emphasize the labial repositioning of a tooth, while simultaneously accomplishing aggressive rotational correction through coupled labial-lingual forces. In this manner, specific and aggressive repositioning of the worst positioned teeth can be accomplished while overall, the removable aligner 20 is generally correcting the positions of the rest of the moderately mal-positioned teeth.

In terms of morphology or anatomy of the human teeth, teeth can be broadly categorized as falling into one of two groups. One group includes paddle-shaped teeth and the other group includes conically-shaped teeth. Anterior tooth can be considered as falling into the paddle-shaped category, and cuspids and bicuspids may be considered as falling into the conically shaped category. The molar teeth may be considered as falling somewhere in between these two classifications. Generally, the cavities formed in the polymeric shell of a conventional aligner can translate corrective forces much more readily to paddle-shaped teeth compared to conically shaped teeth. A conventional aligner tends to lack the ability to establish a foothold on such teeth, particularly if the aligner is formed to transmit a rotational force. To describe this more clearly, in the example above, a couple was created to aggressively correct a maxillary lateral tooth (a paddle-shaped tooth) in terms of rotation. A conical or round, tapered tooth on the other hand does not provide the relatively flat lateral surfaces present in a maxillary lateral tooth. To improve on this limitation, a practitioner may place an orthodontic aligner auxiliary 20 into an opening 26 in the polymeric shell at an optimal point on a generally round tooth to provide the foothold needed by an aligner 20 to better accomplish a difficult rotational correction. For example, even if a tooth is generally conically shaped, the teeth will generally exhibit anatomical features such as notches, fissures and developmental grooves allowing an orthodontic aligner auxiliary 30 to gain rotational contact.

In addition to direct tooth contact to deliver therapeutic forces, on any one single tooth, other embodiments of the present invention perform other useful and treatment-enhancing functions that involve movements of two or more teeth or groups of teeth. For example, one embodiment of the present invention may be used in the following manner. As before, the polymeric shell is first pierced, creating an opening into a cavity, typically accomplished by hand-held pliers or other means of creating an opening 26 into a cavity 24 of predetermined dimensions to positively retain an orthodontic aligner auxiliary 30. The opening 26 may be round, for example, and of a specific diameter. Other embodiments of the orthodontic aligner auxiliary 30 may require that the opening 26 be oval, "race-track"-shaped, rectangular, square and so on. In any case, an orthodontic aligner auxiliary 30 with a shape corresponding to the opening 26 can be retained in the opening 26, thereby producing a positive, stable and dependable retention. Once retained on the polymeric shell in this manner, the orthodontic aligner auxiliary 30 can perform the function of a hook for engaging elastomeric traction, as shown for example in FIG. 9. Sometimes called "rubber bands", such combinations of hooks and elastomeric traction units are very common to all types of orthodontic treatment.

The latitude to position such an elastic hook virtually anywhere on an aligner 20 has great utility to the orthodontist in resolving both minor corrections, as well as basic corrections such as closing or creating spaces. In order to allow a tooth to be moved by an aligner-mounted elastomeric traction hook, an orthodontist typically may cut away a small area of the polymeric shell corresponding to the area in which the tooth is to be pulled and a conventional steel hook may be attached to the tooth to be moved. Without the restrictions of the shell and its tight-fitting cavity, a tooth pulled by such a device along with a rubber band will respond and move into a more desirable position. Once accomplished, the hook can be very easily removed from the shell. Normally, installing and then removing a hook from conventional metallic armamentarium would inevitably require either destroying a component upon removal, or the mechanical bonding of a hook with an orthodontic adhesive and then de-bonding, both of which are time consuming and comparatively expensive. So, one embodiment of the present invention allows a simple and flexible installation of a hook on an aligner.

Figure 10:
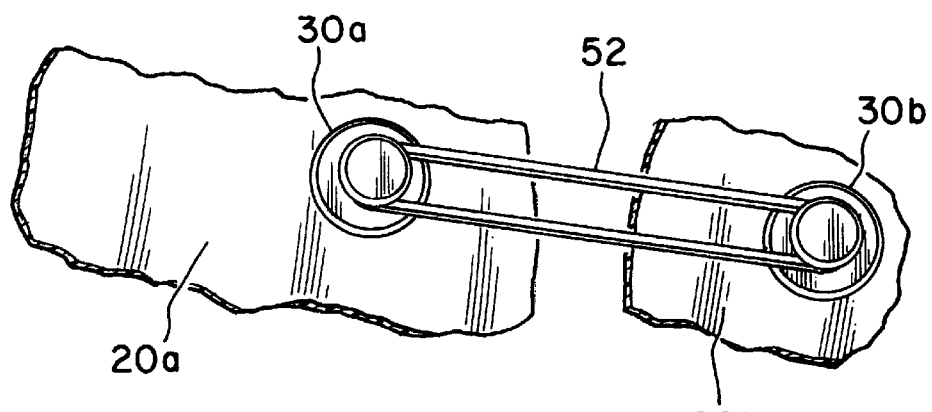
FIG. 10 is a detail perspective view of a rubber band 52 exerting a retractive force between two orthodontic aligner auxiliaries 30a and 30b.
Figure 11:
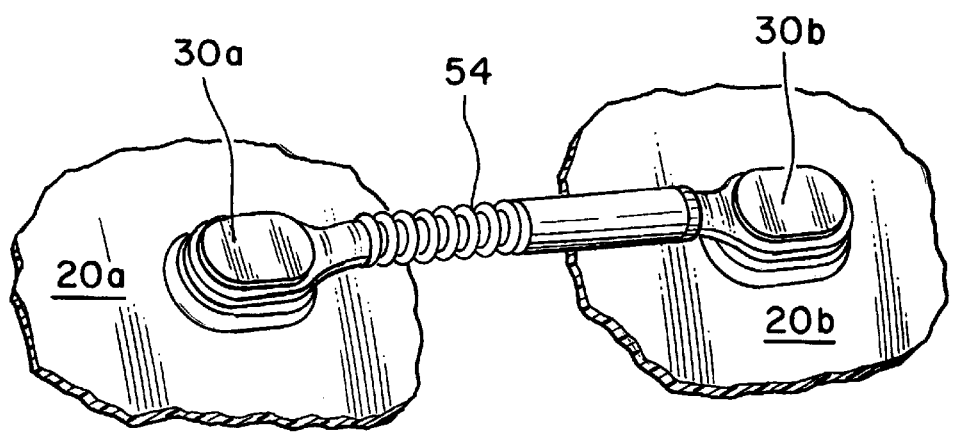
FIG. 11 is a detail perspective view of a spring 54 exerting an expanding force between two orthodontic aligner auxiliaries 30a and 30b.
Figure 12:
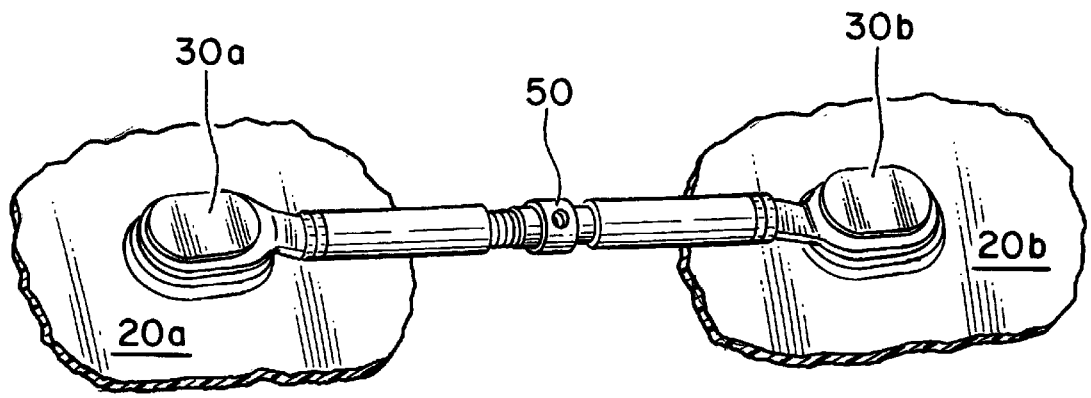
FIG. 12 is a detail perspective view of a connecting device 50 that can be used to exert either an expanding force or a retractive force between two orthodontic aligner auxiliaries 30a and 30b.

Yet other embodiments of the present invention useful for the corrective movement of multiple teeth require that the polymeric shell be modified. For some treatment objectives, groups of teeth 10 must be moved relative to each other. To accomplish this, the aligner 20 may be trimmed so that very little material connects one segment of the shell from another. For some patients, treatment requires that the aligner 20 actually be cut into two separate, disconnected sections 20a and 20b. In both cases, one section of the shell contains cavities engaging one or more teeth to be moved, as does the other section. Orthodontic aligner auxiliaries 30a and 30b are retained in both of the two sections of the aligner 20a and 20b, allowing them to be moved relative to each other. One type of relative movement of the sectioned shells involves retractive forces that draw two sets of teeth together, as shown for example in FIG. 10 using a rubber band 52. Such forces can also be generated using a wide variety of other types of retractive devices, such as flat springs, tension coil springs, threaded systems, magnets, elastomeric units and the like. Expansive forces that move two teeth or two groups of teeth apart can be exerted by means of an expanding device, such as an expansion springs 54 (depicted in FIG. 11), flat springs, drive screws 50 (depicted in FIG. 12), magnets and the like.

As can be appreciated, current orthodontic practice involves several common means for achieving tractive forces as well as expansive forces as described and anyone familiar with those methods and devices will readily understand ways in which such means can be adapted to sectioned aligner-based treatment via attachment methods based on the present invention.

Figure 13A:
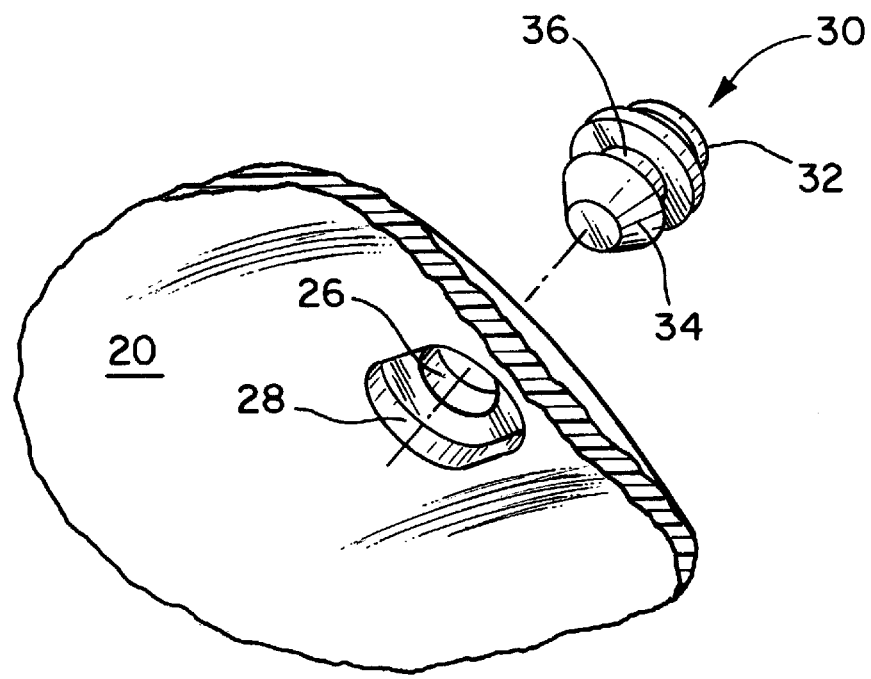
FIGS. 13(a) and 13(b) are detail perspective views of the interior surface of one of the cavities of the aligner 20 showing a recessed land 28 surrounding the opening 26 in the aligner 20, before and after insertion of an orthodontic aligner auxiliary 30.
Figure 13B:
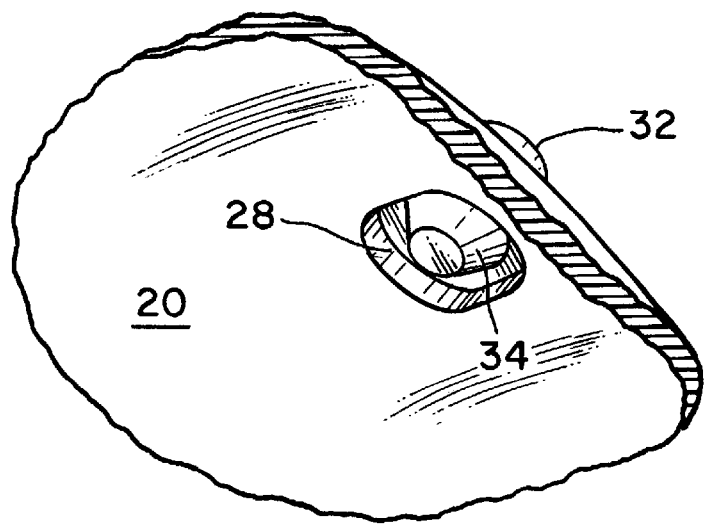

To differentiate the various functions of the present invention, some of the shell-mounted devices of the present invention are described as functioning in a direct, tooth-contacting, tooth-moving manner whereas others such as the hook embodiment described above serve in a non-tooth contacting/tooth-moving function. Since the non-tooth contacting embodiments of the present invention are nonetheless retained in the polymeric shell via a snap fit and extend at least in part through openings in the shell, certain features of the device must be prevented from inadvertent and undesirable tooth contact. To avoid this, hand-held pliers with appropriate dies can be heated and brought into compressive contact with the polymeric shell. Such instruments take advantage of the thermoformable characteristic of the shell polymeric material to form a recessed land 28 locally in the shell, as illustrated in FIGS. 13(a) and 13(b). Another means of producing such recessed lands 28 involve installing patterns on the original stone models so that the lands 28 are automatically pre-formed in the polymeric shell of the aligner 20 as it is originally thermoformed. Such lands 28 can be located at pre-determined ideal positions to receive a non-tooth contacting embodiment of the orthodontic aligner auxiliary 30 as selected by the orthodontist. By creating a small raised land 28, and by placing the opening 26 into a cavity 24 on the land 28, an orthodontic aligner auxiliary 30 can be retained in the shell with the tip portions 34 of the orthodontic aligner auxiliary 30 held clear of the tooth surface. This prevents any inadvertent and undesirable tooth movement from occurring. The orthodontic aligner auxiliaries 30 used in this embodiment may have inwardly projecting tips that are blunted to reduce the required height of the land 28.

In the case of a device being retained in an opening 26 located on an outwardly projecting land 28, the physical, outside dimension of the land 28 itself may be capable of providing additional stability and retention beyond that achievable just by the groove-based retention within the opening 26 as described above. In such an embodiment, the inwardly-facing side of the orthodontic aligner auxiliary 30 would have land-accommodating features in addition to the tapered features and the groove-type retention in the opening. The additional support and stability imparted to the orthodontic aligner auxiliary 30 would dissipate forces and hold the device in a more stable orientation on the outer surface of the aligner 20. Additional support may be necessary in the case of an orthodontic aligner auxiliary 30 serving in the role of a hook, where a stout, high-pull elastic is engaged to it. Such a device/land inter-fit would also be further structurally enhanced via the use of bonding, where adhesive is positioned and cured in the interface between the outside surfaces of a formed land 28 and the inwardly facing concave and accommodating features of the orthodontic aligner auxiliary 30.

In the foregoing, the descriptions of the various embodiments and functions of the present invention have been generally described as accomplishing correction of an individual tooth and corrections involving multiple teeth. A third broad category of applications for which the present invention is directed involves improving aligner-based treatment modality in general. In order to be effective, aligners 20 must at all times remain fully seated on a patient's arches. Since the biasing of the cavities 24 tends to cause an aligner 20 to lift off of the teeth 10, an embodiment of the present invention functions to insure that the entire aligner 20 is retained on the teeth 10 in the desired, fully-seated position at all times. For this purpose, a number of orthodontic aligner auxiliaries 30 can may be placed at positions around an upper or lower aligner 20 at points best suited for appliance retention. The orthodontic aligner auxiliaries 30 are positioned on the aligner 20 closer to its gingival edge and at locations where the orthodontic aligner auxiliaries 30 will project inwardly into the interproximal spaces between teeth 10, as illustrated in FIG. 14. Since teeth 10 are generally bell-shaped, and particularly since the spaces between teeth 10 provide a mechanical undercut, the inwardly-projecting tips of the orthodontic aligner auxiliaries 30 can find a positive, retentive foothold. With the orthodontic aligner auxiliaries 30 located as described, the aligner 20 is first partially seated on the teeth 10 and due to tooth contact, the retentive points first cause the labial or lingual sides of the shell of the aligner 20 to flex outward. As the aligner 20 becomes fully seated, the retentive tips of the orthodontic aligner auxiliaries 30 find their intended positions closer to the gum between the teeth 10, allowing the sides of the aligner 20 to return to their passive configuration, thus positively forcing the retentive tips of the orthodontic aligner auxiliaries 30 to wedge into their intended retentive undercut positions.

Another useful application of the present invention involves the use of orthodontic aligner auxiliaries 30 as x-ray markers. At several points during orthodontic treatment as well as for pre-treatment planning, it is useful for an orthodontist to take lateral x-rays of the patient's head. Sometimes called "head plates," such x-rays allow the orthodontist to analyze the positions of the roots relative to each other and relative to the supporting alveolar bone. Sometimes difficulty is encountered associating structure seen on an x-ray with the actual oral anatomy. In such cases, one or more of the orthodontic aligner auxiliaries 30 can be formed from a plastic that is blended with a radio-opaque filler such as magnesium dioxide in a ratio of about 35 parts per million. Such an addition allows the orthodontic aligner auxiliary 30 to serve as a convenient marker. An orthodontist in this case would install a marker device on an aligner 20 in the general region of scrutiny. Such markers then would provide a physical reference from which to ascertain the exact location of features seen on an x-ray image.

In addition, radio-opacity is useful as a safety feature in general. For example, the polymeric shell of an aligner 20 can be cut into two pieces, as previously discussed. Sometimes aligners 20 are formed to conform only to the front teeth and these too can be trimmer smaller. As a result, aligners 20 can become sufficiently small to be aspirated by a patient. If an aligner 20 is aspirated and it becomes necessary to surgically remove the aligner 20, its position within the patient's airway or lungs can first be ascertained by x-ray imaging if the aligner 20 has been formed with a radio-opaque additive or radio-opaque marker.

The present invention can also be useful in other fields that are not directly related to tooth movement. Orthodontists historically have rated the factor of patient cooperation as one of the most important factors in determining the quality of the finished result of orthodontic treatment. If patients do not follow the orthodontist's instructions for hygiene, replacement of rubber bands, activation of an appliance mechanism, or even basic use of an appliance, the treatment assumptions regarding response and progress of treatment can be negated. Orthodontists have resorted to all sorts of means to get patients positively involved in their treatment and therefore more likely to be cooperative. One successful tactic has been to provide means for the patient's treatment to serve as a vehicle for self-expression. For example, many of the urethane elastomeric materials common in treatment are available in a wide variety of colors, including glow-in-the-dark versions. These modalities have been very successful in adding fun to otherwise aversive aspects of treatment, and therefore the essential element of patient cooperation. As described above, embodiments of the present invention can be offered in the same, currently available series of colors. Additionally, the orthodontic aligner auxiliaries can be produced in ornamental or decorative shapes and profiles 60, as shown for example in FIGS. 15a and 15b, so that when retained by the aligner 20 display such things as astrological signs and other symbols that again could be offered in both a series of colors and glow-in-the-dark variations.

Another similar embodiment that may serve as a vehicle for self-expression by the patient are devices that contain a micro-sized sealed battery and a light-emitting diode or other light source. One can only marvel at the excitement that a young orthodontic patient would enjoy through showing various colored or flashing lights on his braces to his or her friends. Orthodontists make no exceptions in using any tools at their disposal to gain a cooperative attitude from their patients and a cooperative attitude can positively impact treatment results as much as any functional device or innovative treatment method.

The above disclosure sets forth a number of embodiments of the present invention. Other arrangements or embodiments, not precisely set forth, could be practiced under the teachings of the present invention and as set forth in the following claims.

I claim:

1. An apparatus for orthodontic treatment comprising:
   a removable orthodontic aligner having a polymeric shell with a plurality of cavities shaped to receive teeth, said shell having at least one opening extending through the shell from a cavity; and
   an orthodontic aligner auxiliary inserted through and retained by the opening in the shell of the orthodontic aligner by a snap fit to exert a therapeutic force on a tooth.

2. The apparatus of claim 1 wherein the orthodontic aligner auxiliary further comprises:
   a nut securable by a snap fit to the opening in the shell of the orthodontic aligner and having a threaded hole; and
   a screw having a threaded portion to adjustably engage the nut.

3. The apparatus of claim 1 wherein the orthodontic aligner auxiliary is bonded to the opening in the shell.

4. The apparatus of claim 1 wherein the orthodontic aligner auxiliary comprises a protrusion extending through the opening and into the cavity of the shell to contact and exert a therapeutic force on a tooth.

5. The apparatus of claim 1 wherein the orthodontic aligner auxiliary comprises a plurality of removable tacks of progressive length, wherein each tack can be secured to and removed from the opening in the shell in a predetermined sequence over time, thereby exerting a progression of therapeutic forces on a tooth.

6. The apparatus of claim 1 wherein the orthodontic aligner auxiliary comprises a plurality of removable tacks having progressive elasticities, wherein each tack can be secured to and removed from the opening in the shell in a predetermined sequence over time, thereby exerting a progression of therapeutic forces on a tooth.

7. The apparatus of claim 1 wherein the opening extends through the shell, and wherein the orthodontic aligner auxiliary comprises:
   a head larger than the opening in the shell;
   a circumferential groove to engage the opening in the shell; and
   a tip insertable through the opening in the shell so that the circumferential groove engages the opening.

8. The apparatus of claim 7 wherein the tip is tapered.

9. The apparatus of claim 1 further comprising an ornamental attachment securable to the opening in the shell.

10. The apparatus of claim 1 wherein the orthodontic aligner auxiliary further comprises a radio-opaque marker.

11. The apparatus of claim 1 wherein the shell has a plurality of openings extending from a tooth, with orthodontic aligner auxiliaries secured to each opening to exert a couple on the tooth.

12. The apparatus of claim 1 wherein the orthodontic aligner auxiliary further comprises a protrusion extending into the interproximal space between adjacent teeth and exerting a retentive force to hold the shell fully seated on the teeth.

13. An apparatus for orthodontic treatment comprising:
   a removable orthodontic aligner having a polymeric shell with a plurality of cavities shaped to receive teeth, said orthodontic aligner having:
      (a) a first segment for engaging a first set of teeth having at least one opening;
      (b) a second segment movable relative to the first segment for engaging a second set of teeth and having at least one opening;
   a first orthodontic aligner auxiliary securable to the opening in the first segment;
   a second orthodontic aligner auxiliary securable to the opening in the second segment; and a connecting member extending between the first orthodontic aligner auxiliary and the second orthodontic aligner auxiliary to exert a therapeutic force on the first and second sets of teeth.

14. The apparatus of claim 13 wherein said connecting member comprises a retractive device.

15. The apparatus of claim 13 wherein said connecting member comprises an expanding device.

16. A method of orthodontic treatment comprising:
    forming a removable orthodontic aligner having a polymeric shell with a plurality of cavities shaped to receive teeth
    creating at least one opening extending through the shell of the orthodontic aligner from a cavity; and
    inserting an orthodontic aligner auxiliary through the opening in the shell of the orthodontic aligner so that the orthodontic aligner auxiliary is retained in the opening by a snap fit and exerts a therapeutic force on a tooth.

17. The method of claim 16 wherein the orthodontic aligner auxiliary is bonded to the opening in the shell.

18. The method of claim 16 further comprising the step of plastically deforming the shell adjacent to the opening.

19. A method of orthodontic treatment comprising:
    providing a removable orthodontic aligner having a polymeric shell with a plurality of cavities shaped to receive teeth, said orthodontic aligner having a first segment for engaging a first set of teeth and a second segment for engaging a second set of teeth; said first and second segments being movable relative to one another;
    creating a first opening in the first segment of the orthodontic aligner;
    creating a second opening in the second segment of the orthodontic aligner;
    securing a first orthodontic aligner auxiliary to the first opening;
    securing a second orthodontic aligner auxiliary to the second opening; and
    attaching a connecting member between the first orthodontic aligner auxiliary and the second orthodontic aligner auxiliary to exert a therapeutic force on the first and second sets of teeth.

20. The method of claim 19 wherein the connecting member comprises a retractive device.

21. The method of claim 19 wherein the connecting member comprises an expanding device.

22. A method of orthodontic treatment comprising:
    forming a removable orthodontic aligner having a polymeric shell with a plurality of cavities shaped to receive teeth
    creating at least one opening extending into the shell of the orthodontic aligner from a cavity; and
    removably securing each of a plurality of orthodontic aligner auxiliaries to the opening in the shell of the orthodontic aligner in a predetermined sequence over time, whereby said orthodontic aligner auxiliaries exert a progression of therapeutic forces on a tooth.

23. The method of claim 22 wherein the orthodontic aligner auxiliaries comprise a plurality of removable tacks of progressive length.

24. The method of claim 22 wherein the orthodontic aligner auxiliaries comprise a plurality of removable tacks having progressive elasticities.

25. An apparatus for orthodontic treatment comprising:
    a removable orthodontic aligner having a polymeric shell with a plurality of cavities shaped to receive teeth, said shell having at least one opening extending through the shell into a cavity; and
    a tack removably insertable through and being retained by the opening in the shell by a snap fit to exert a therapeutic force on a tooth, said tack having:
    (a) a tip larger than the opening in the shell, but insertable through the opening by exertion of an external force to temporarily distend the opening; and
    (b) a head larger than the opening in the shell, thereby engaging the shell between the tip and head of the tack after insertion of the tip through the opening.

26. The apparatus of claim 25 wherein the tack is comprised of a resilient polymer.

27. The apparatus of claim 25 wherein the tack is inserted from the cavity through the opening in the shell with the head remaining in the cavity to exert a therapeutic force on a tooth.

28. The apparatus of claim 25 wherein the tip of the tack is inserted through the opening in the shell into the cavity to exert a therapeutic force on a tooth.

29. The apparatus of claim 25 wherein the tack further comprises a circumferential groove between the tip and head to engage the opening in the shell.

30. The apparatus of claim 25 wherein the tip of the tack is tapered.

* * * * *